(12) United States Patent
Higashiura et al.

(10) Patent No.: US 8,222,419 B2
(45) Date of Patent: Jul. 17, 2012

(54) OXEPIN DERIVATIVE

(75) Inventors: Kunihiko Higashiura, Kato (JP); Takashi Ogino, Kato (JP); Kazuhito Furukawa, Kato (JP); Yuriko Yamazaki, Kato (JP)

(73) Assignee: Nippon Zoki Pharmaceutical Co., Ltd., Osaka-Shi (JP)

( * ) Notice: Subject to any disclaimer, the term of this patent is extended or adjusted under 35 U.S.C. 154(b) by 76 days.

(21) Appl. No.: 12/311,215

(22) PCT Filed: Sep. 27, 2007

(86) PCT No.: PCT/JP2007/068804
§ 371 (c)(1),
(2), (4) Date: Mar. 23, 2009

(87) PCT Pub. No.: WO2008/038711
PCT Pub. Date: Apr. 3, 2008

(65) Prior Publication Data
US 2010/0004456 A1    Jan. 7, 2010

(30) Foreign Application Priority Data
Sep. 29, 2006   (JP) .................................. 2006-268640

(51) Int. Cl.
*C07D 401/00* (2006.01)
(52) U.S. Cl. ...................................................... 546/196
(58) Field of Classification Search .................... 546/196
See application file for complete search history.

(56) References Cited

U.S. PATENT DOCUMENTS

| 4,086,350 | A | 4/1978 | Zirkle |
| 4,396,550 | A | 8/1983 | Takizawa et al. |
| 4,412,999 | A | 11/1983 | Remy et al. |
| 4,465,835 | A | 8/1984 | Takizawa et al. |
| 4,522,821 | A | 6/1985 | Remy et al. |
| 4,596,804 | A | 6/1986 | Takizawa et al. |
| 4,912,222 | A | 3/1990 | Griffith et al. |
| 5,416,087 | A | 5/1995 | Wong et al. |
| 7,317,026 | B2 * | 1/2008 | Edgar et al. ............. 514/320 |
| 7,589,103 | B2 * | 9/2009 | Carson et al. ............ 514/304 |
| 2005/0009860 | A1 | 1/2005 | Carson et al. |
| 2005/0143348 | A1 | 6/2005 | Edgar et al. |
| 2005/0288283 | A1 * | 12/2005 | Hellberg ............... 514/232.5 |

FOREIGN PATENT DOCUMENTS

| GB | 1128734 | 10/1968 |
| JP | A-51-70768 | 6/1976 |
| JP | A-56-150082 | 11/1981 |
| JP | A-58-188879 | 11/1983 |
| JP | A-60-28972 | 2/1985 |
| JP | A-3-500053 | 1/1991 |
| JP | A-6-116273 | 4/1994 |
| JP | A-7-41481 | 2/1995 |
| WO | WO 92/06970 | 4/1992 |
| WO | WO 2005/003131 A1 | 1/2005 |

OTHER PUBLICATIONS

Nov. 15, 2010 European Search Report issued in EP 07 82 8550.

\* cited by examiner

*Primary Examiner* — Nizal Chandrakumar
(74) *Attorney, Agent, or Firm* — Oliff & Berridge, PLC

(57) ABSTRACT

The present invention provides a compound, an oxepin derivative having excellent histamine receptor antagonistic action, which is useful as an antihistamine. The oxepin derivative of the present invention has a potent histamine receptor antagonistic action. Further, the compound of the present invention shows low intracerebral migration even when a mouse that is orally administered with the compound is subjected to an intracerebral receptor binding test, so that the compound has preferred properties of alleviating side effects in the central nervous system, such as drowsiness. The oxepin derivative of the present invention is very useful as a novel antihistamine having smaller side effects in the central nervous system, such as drowsiness.

15 Claims, No Drawings

OXEPIN DERIVATIVE

TECHNICAL FIELD

The present invention relates to an oxepin derivative and salt and hydrate thereof that are pharmaceutically acceptable, which are useful as antihistamines.

BACKGROUND ART

Histamines are representative chemical mediators that induce allergic reactions, and the histamines are released from cells such as mast cells and basocytes when substances that are causative of allergy are entered into the body. The released histamines are bound to a histamine type 1 receptor (H1 receptor) protein to exhibit pharmacological actions such as hypotension, vascular hyperpermeability, constriction of smooth muscles, vasodilatation, or glandular hypersecretion, and involved in the manifestation of allergic reactions and inflammations. As described above, histamines are related to various diseases of human, and the allergic diseases and inflammations can be prevented or cured by controlling their actions. Agents for controlling histamine release and agents for inhibiting the binding of histamines with receptors (antihistamines) are numerously commercially available, and the agents are used in diseases such as bronchial asthma, allergic rhinitis, pollinosis, urticaria, and atopic dermatitis.

However, antihistamines that are conventionally known exhibit some undesired side effects such as sedative action, drowsiness, dizziness, and malaise, based on the actions on the central nervous system; and dry mouth, mucosal dryness, and visual impairment, based on the anti-cholinergic actions; therefore, there are some limitations of use such as prohibition of taking histamines before driving automobiles, which in turn cause inconvenience in use. For these reasons, antihistamines which are free from such problems and have excellent effects are in demand from the patients and the medicinal sites.

In view of the above, as a result of intensive studies, the present inventors have found the oxepin derivative of the present invention having smaller side effects of the central nervous system and potent antihistamine action. The oxepin derivatives have been known to have anti-asthmatic action (see Patent Publication 1); dopamine antagonistic action (see Patent Publication 2); δ-opioid regulatory action (see Patent Publication 3); and the like; however, the derivatives that have smaller side effects in the central nervous system such as drowsiness, and potent antihistamine actions, as in the compounds of the present invention, have not been known.

Patent Publication 1: Japanese Patent Laid-Open No. Sho 56-150082
Patent Publication 2: Japanese Patent Laid-Open No. Sho 58-188879
Patent Publication 3: WO 2005/003131

DISCLOSURE OF THE INVENTION

Problems to be Solved by the Invention

An object of the present invention is to provide a useful compound that has smaller side effects in the central nervous system, such as drowsiness, and excellent antihistamine action.

Means to Solve the Problems

As a result of intensive studies on antihistamine compounds having the characteristics mentioned above, the present inventors have found that an oxepin derivative represented by the structural formula (I) given below is a compound useful as a medicament that has excellent antihistamine action and alleviates side effects in the central nervous system, such as drowsiness. The present invention has been perfected thereby.

Effects of the Invention

The oxepin derivative of the present invention has an excellent antagonistic action for histamine receptors and shows low intracerebral migration even when a mouse that is orally administered with the compound is subjected to an intracerebral receptor binding test, and alleviates side effects in the central nervous system, such as drowsiness. Therefore, the oxepin derivative has properties desired for medicaments such as antihistamines, and is highly useful.

BEST MODE FOR CARRYING OUT THE INVENTION

The present invention relates to an oxepin derivative, and salt and hydrate thereof that are pharmaceutically acceptable, wherein the oxepin derivative is represented by the following general formula (I):

[Ka 1]

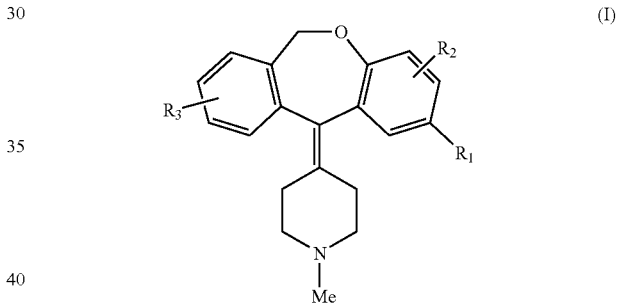

(I)

wherein $R_1$ is a hydrogen, a halogen, a formyl, a carbonitrile, a tetrazolyl, a carboxyl, a hydroxyalkyl, a carboxyalkyl, an alkoxycarbonylalkyl, an alkoxycarbonyl, a hydroxyalkylaminocarbonyl, an alkoxycarbonylalkylaminocarbonyl, a hydroxyalkenyl, a carboxyalkenyl, an alkoxycarbonylalkenyl, a ureido, an alkylcarbonylamino, or an aminoalkyl which may be substituted by one or two substituents selected from the following (a) to (e):
(a) an alkylcarbonyl;
(b) an alkoxycarbonyl;
(c) a carboxyalkylcarbonyl;
(d) an alkoxycarbonylalkylcarbonyl; and
(e) a benzoyl;
$R_2$ is a substituent at 3-position or 4-position of the dibenzoxepin backbone, and stands for a hydrogen, a halogen, a carbonitrile, a carboxyl, a carboxyalkyl, an alkoxycarbonyl, a hydroxyalkylaminocarbonyl, a carboxyalkenyl, or an alkoxycarbonylalkenyl, with proviso that the halogen and the carboxyl each is substituted only at 4-position; and $R_3$ is a substituent at 8-position or 9-position of the dibenzoxepin backbone, and stands for a hydrogen, a carboxyl, an alkoxycarbonyl, or a hydroxyalkylaminocarbonyl,
wherein one of $R_1$, $R_2$ and $R_3$ stands for the substituent as defined above other than the hydrogen, and the remaining two stand for a hydrogen.

In addition, the present invention relates to a medicament such as an antihistamine containing, as an active ingredient, an oxepin derivative, and salt and hydrate thereof that are pharmaceutically acceptable, wherein the oxepin derivative is represented by the following general formula (I'):

[Ka 2]

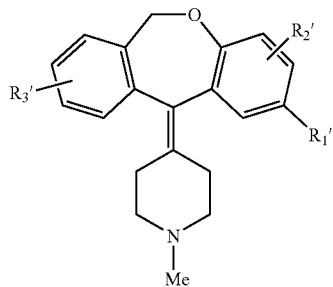

(I')

wherein $R_1{}'$ is a hydrogen, a halogen, a formyl, a carbonitrile, a tetrazolyl, a carboxyl, an alkyl, a hydroxyalkyl, a carboxyalkyl, an alkoxycarbonylalkyl, an alkoxycarbonyl, a hydroxyalkylaminocarbonyl, an alkoxycarbonylalkylaminocarbonyl, a hydroxyalkenyl, a carboxyalkenyl, an alkoxycarbonylalkenyl, a ureido, an alkylcarbonylamino, or an aminoalkyl which may be substituted by one or two substituents selected from the following (a) to (e):
(a) an alkylcarbonyl;
(b) an alkoxycarbonyl;
(c) a carboxyalkylcarbonyl;
(d) an alkoxycarbonylalkylcarbonyl; and
(e) a benzoyl;
$R_2{}'$ is a substituent at 3-position or 4-position of the dibenzoxepin backbone, and stands for a hydrogen, a halogen, a carbonitrile, a carboxyl, a carboxyalkyl, an alkoxycarbonyl, a hydroxyalkylaminocarbonyl, a carboxyalkenyl, or an alkoxycarbonylalkenyl; and
$R_3{}'$ is a substituent at 8-position or 9-position of the dibenzoxepin backbone, and stands for a hydrogen, a carboxyl, an alkoxycarbonyl, or a hydroxyalkylaminocarbonyl, wherein one of $R_1{}'$, $R_2{}'$ and $R_3{}'$ stands for the substituent as defined above other than the hydrogen, and the remaining two stand for a hydrogen.

In the above-mentioned general formulas (I) and (I'), the term "alkyl" stands for a linear or branched alkyl group having 1 to 4 carbon atoms, and the alkyl group is preferably a methyl, an ethyl, a propyl, an isopropyl, a butyl, an isobutyl, a sec-butyl, a tert-butyl, or the like.

The term "alkoxy" stands for a linear or branched alkoxy group having 1 to 4 carbon atoms, and the alkoxy group is preferably a methoxy, an ethoxy, a propyloxy, an isopropyloxy, a butyloxy, or the like.

The term "alkenyl" stands for a linear or branched alkenyl group having 1 to 4 carbon atoms, and the alkenyl group is preferably a vinyl, an allyl, a propenyl, an isopropenyl, a 1-butenyl, a 2-butenyl, or the like.

The aminoalkyl of $R_1$ or $R_1{}'$ may be substituted by one or two substituents selected from the above-mentioned (a) to (e), and each substituent is substituted at an amino group moiety of the aminoalkyl.

Among the compounds of the present invention, especially preferred compounds are as follows.
11-(1-Methylpiperidin-4-ylidene)-6,11-dihydrodibenz[b,e]oxepin-2-carboxylic acid [Compound 1]
Ethyl 11-(1-methylpiperidin-4-ylidene)-6,11-dihydrodibenz[b,e]oxepin-2-carboxylate hydrochloride [Compound 2]
Ethyl {[11-(1-methylpiperidin-4-ylidene)-6,11-dihydrodibenz[b,e]oxepin-2-carbonyl]amino}acetate [Compound 3]
4-(2-Bromo-6H-dibenz[b,e]oxepin-11-ylidene)-1-methylpiperidine [Compound 4]
11-(1-Methylpiperidin-4-ylidene)-6,11-dihydrodibenz[b,e]oxepin-2-carbonitrile [Compound 5]
Methyl 3-[11-(1-methylpiperidin-4-ylidene)-6,11-dihydrodibenz[b,e]oxepin-2-yl]acrylate hydrochloride [Compound 6]
3-[11-(1-Methylpiperidin-4-ylidene)-6,11-dihydrodibenz[b,e]oxepin-2-yl]acrylic acid [Compound 7]
1-Methyl-4-[2-(2H-tetrazol-5-yl)-6H-dibenz[b,e]oxepin-11-ylidene]piperidine [Compound 8]
tert-Butyl [11-(1-methylpiperidin-4-ylidene)-6,11-dihydrodibenz[b,e]oxepin-2-ylmethyl]carbamate [Compound 9]
N-[11-(1-Methylpiperidin-4-ylidene)-6,11-dihydrodibenz[b,e]oxepin-2-yl]acetamide [Compound 10]
C-[11-(1-Methylpiperidin-4-ylidene)-6,11-dihydrodibenz[b,e]oxepin-2-yl]methylamine dihydrochloride [Compound 11]
4-(3-Bromo-6H-dibenz[b,e]oxepin-11-ylidene)-1-methylpiperidine [Compound 12]
11-(1-Methylpiperidin-4-ylidene)-6,11-dihydrodibenz[b,e]oxepin-3-carbonitrile [Compound 13]
Ethyl [11-(1-methylpiperidin-4-ylidene)-6,11-dihydrodibenz[b,e]oxepin-2-ylmethyl]carbamate [Compound 14]
N-[11-(1-Methylpiperidin-4-ylidene)-6,11-dihydrodibenz[b,e]oxepin-2-ylmethyl]acetamide [Compound 15]
1-Methyl-4-(2-methyl-6H-dibenz[b,e]oxepin-11-ylidene)-piperidine [Compound 16]
[11-(1-Methylpiperidin-4-ylidene)-6,11-dihydrodibenz[b,e]oxepin-2-yl]urea [Compound 17]
11-(1-Methylpiperidin-4-ylidene)-6,11-dihydrodibenz[b,e]oxepin-3-carboxylic acid [Compound 18]
N-(2-Hydroxyethyl)-11-(1-methylpiperidin-4-ylidene)-6,11-dihydrodibenz[b,e]oxepin-2-carboxamide [Compound 19]
N-[11-(1-Methylpiperidin-4-ylidene)-6,11-dihydrodibenz[b,e]oxepin-2-ylmethyl]benzamide [Compound 20]
[11-(1-Methylpiperidin-4-ylidene)-6,11-dihydrodibenz[b,e]oxepin-2-yl]methanol [Compound 21]
3-[11-(1-Methylpiperidin-4-ylidene)-6,11-dihydrodibenz[b,e]oxepin-2-yl]prop-2-en-1-ol hydrochloride [Compound 22]
11-(1-Methylpiperidin-4-ylidene)-6,11-dihydrodibenz[b,e]oxepin-2-carboaldehyde [Compound 23]
[11-(1-Methylpiperidin-4-ylidene)-6,11-dihydrodibenz[b,e]oxepin-2-yl]acetic acid [Compound 24]
Ethyl [11-(1-methylpiperidin-4-ylidene)-6,11-dihydrodibenz[b,e]oxepin-2-yl]acetate [Compound 25]
N-[11-(1-Methylpiperidin-4-ylidene)-6,11-dihydrodibenz[b,e]oxepin-2-ylmethyl]succinamic acid [Compound 26]
Ethyl N-[11-(1-methylpiperidin-4-ylidene)-6,11-dihydrodibenz[b,e]oxepin-2-ylmethyl]succinamate [Compound 27]
11-(1-Methylpiperidin-4-ylidene)-6,11-dihydrodibenz[b,e]oxepin-9-carboxylic acid [Compound 28]
Ethyl 11-(1-methylpiperidin-4-ylidene)-6,11-dihydrodibenz[b,e]oxepin-9-carboxylate [Compound 29]
4-(4-Bromo-6H-dibenz[b,e]oxepin-11-ylidene)-1-methylpiperidine [Compound 30]
Ethyl 3-[11-(1-methylpiperidin-4-ylidene)-6,11-dihydrodibenz[b,e]oxepin-4-yl]acrylate [Compound 31]

3-[11-(1-Methylpiperidin-4-ylidene)-6,11-dihydrodibenz[b,e]oxepin-4-yl]acrylic acid [Compound 32]
11-(1-Methylpiperidin-4-ylidene)-6,11-dihydrodibenz[b,e]oxepin-8-carboxylic acid [Compound 33]
11-(1-Methylpiperidin-4-ylidene)-6,11-dihydrodibenz[b,e]oxepin-4-carbonitrile [Compound 34]
Ethyl 3-[11-(1-methylpiperidin-4-ylidene)-6,11-dihydrodibenz[b,e]oxepin-3-yl]acrylate [Compound 35]
Ethyl 11-(1-methylpiperidin-4-ylidene)-6,11-dihydrodibenz[b,e]oxepin-4-carboxylate [Compound 36]
11-(1-Methylpiperidin-4-ylidene)-6,11-dihydrodibenz[b,e]oxepin-4-carboxylic acid [Compound 37]
[11-(1-Methylpiperidin-4-ylidene)-6,11-dihydrodibenz[b,e]oxepin-3-yl]acetate hydrochloride [Compound 38]
11-(1-Methylpiperidin-4-ylidene)-6,11-dihydrodibenz[b,e]oxepin-3-carboxylic acid(2-hydroxyethyl)amide [Compound 39]
11-(1-Methylpiperidin-4-ylidene)-6,11-dihydrobenz[b,e]oxepin-8-carboxylic acid(2-hydroxyethyl)amide [Compound 40]
2- [11-(1-Methylpiperidin-4-ylidene)-6,11-dihydrodibenz[b,e]oxepin-2-yl]propionate hydrochloride [Compound 41]
11-(1-Methylpiperidin-4-ylidene)-6,11-dihydrodibenz[b,e]oxepin-9-carboxylic acid(2-hydroxyethyl)amide [Compound 42]
3-[11-(1-Methylpiperidin-4-ylidene)-6,11-dihydrodibenz[b,e]oxepin-2-yl]propionate hydrochloride [Compound 43]

Among the compounds of the present invention listed above, more preferred compounds include 11-(1-methylpiperidin-4-ylidene)-6,11-dihydrodibenz[b,e]oxepin-2-carboxylic acid [Compound 1], 3-[11-(1-methylpiperidin-4-ylidene)-6,11-dihydrodibenz[b,e]oxepin-2-yl]acrylic acid [Compound 7], [11-(1-methylpiperidin-4-ylidene)-6,11-dihydrodibenz[b,e]oxepin-2-yl]urea [Compound 17], [11-(1-methylpiperidin-4-ylidene)-6,11-dihydrodibenz[b,e]oxepin-2-yl]acetic acid [Compound 24], and 3-[11-(1-methylpiperidin-4-ylidene)-6,11-dihydrodibenz[b,e]oxepin-2-yl]propionate hydrochloride [Compound 43].

The preferred embodiment of the present invention are given hereinbelow.
(1) An oxepin derivative, and salt and hydrate thereof that are pharmaceutically acceptable, wherein the oxepin derivative is represented by the above-mentioned general formula (I).
(2) The oxepin derivative according to the above (1), wherein $R_3$ is a hydrogen.
(3) The oxepin derivative according to the above (2), wherein $R_2$ is a hydrogen.
(4) The oxepin derivative according to the above (3), wherein $R_1$ is a ureido group.
(5) The oxepin derivative according to the above (3), wherein $R_1$ is a carboxyalkyl group.
(6) The oxepin derivative according to the above (5), wherein $R_1$ is a carboxymethyl group or a carboxyethyl group.
(7) The oxepin derivative according to the above (3), wherein $R_1$ is a carboxyl group.
(8) An antihistamine containing, as an active ingredient, an oxepin derivative, and salt and hydrate thereof that are pharmaceutically acceptable, wherein the oxepin derivative is represented by the above-mentioned general formula (I').
(9) The antihistamine according to the above (8), wherein $R_3'$ is a hydrogen.
(10) The antihistamine according to the above (9), wherein $R_2'$ is a hydrogen.
(11) The antihistamine according to the above (10), wherein $R_1'$ is a ureido group.
(12) The antihistamine according to the above (10), wherein $R_1'$ is a carboxyalkyl group.
(13) The antihistamine according to the above (12), wherein $R_1'$ is a carboxymethyl group or a carboxyethyl group.
(13) The antihistamine according to the above (9), wherein $R_1'$ is a carboxyl group.

A general method for producing the compound of the present invention will be given hereinbelow. The compound of the present invention represented by the above-mentioned general formula (I) can be produced according to the method described below. Here, it is obvious for one of ordinary skill in the art that the exact methods usable in the production of specified compounds can vary depending upon their chemical structures.

The compound of the general formula (I) can be obtained by a coupling reaction or a carbonylation reaction using a palladium catalyst of the compound of the general formula (II). For example, a cyanation reaction can be carried out with ligands such as DPPF (1,1'-bis(diphenylphosphino)ferrocene), PPh$_3$ (triphenylphosphine), and P(o-tol)$_3$(tris(2-methylphenyl)phosphine) by using copper cyanide, zinc cyanide, iron ferrocyanide, or sodium cyanide, in the presence of Pd$_2$(dba)$_3$ (dipalladium(0) tris(dibenzylidene acetone)), Pd(OAc)$_2$ (palladium(II) acetate), Pd(PPh$_3$)$_4$ (palladium(O) tetrakis(triphenylphosphine)). The reaction can be carried out in a compatible solvent, such as DMF (dimethylformamide), water, acetone, acetonitrile, or a mixture thereof, at a suitable temperature, preferably at a temperature between room temperature and a boiling point of the solvent.

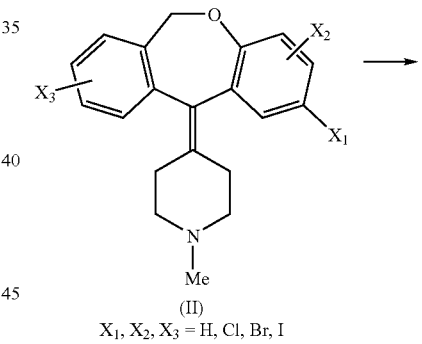

[Ka 3]

(II)
X$_1$, X$_2$, X$_3$ = H, Cl, Br, I

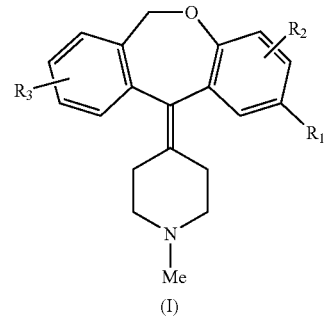

(I)

The compound of the general formula (II) is obtained by a coupling reaction or a Grignard reaction using a titanium chloride of the compound of the general formula (III). For example, the reaction can be carried out by using 4-chloro-N-methylpiperidine, and preparing a Grignard reagent with magnesium. The reaction can be carried out in a compatible solvent, such as THF (tetrahydrofuran), ether, or a mixture thereof, at a suitable temperature, preferably a temperature between 0° C. and a boiling point of the solvent.

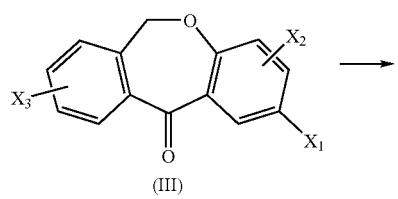

(III)

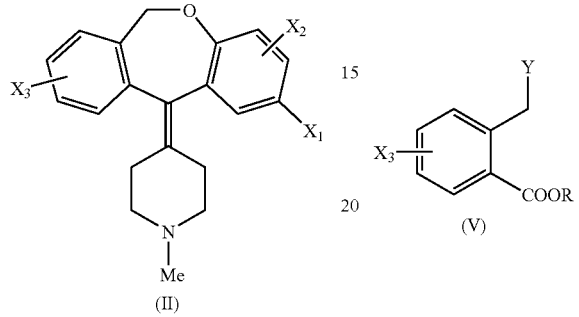

(II)

The compound of the general formula (III) is obtained by an intramolecular Friedel-Crafts reaction of the compound of the general formula (IV). The reaction can be carried by using aluminum chloride, $BF_3 \cdot OEt_2$ (boron trifluoride-diethyl ether complex), titanium chloride, tin chloride, or polyphosphoric acid as a Lewis acid, in a compatible solvent such as nitrobenzene, carbon disulfide, dichloroethane, xylene, or a mixture thereof, at a suitable temperature, preferably a temperature between room temperature and a boiling point of the solvent.

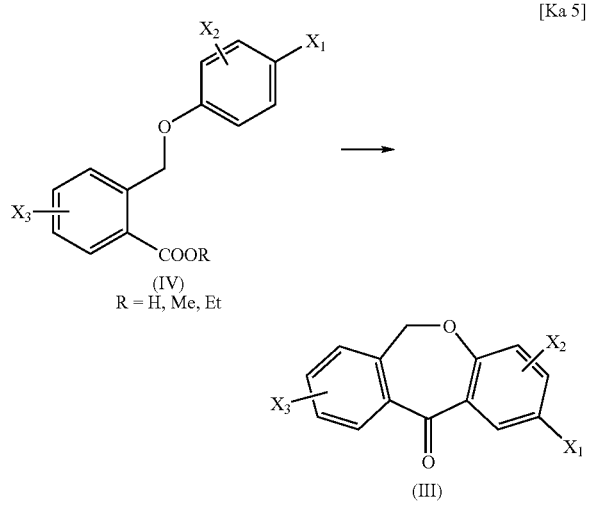

The compound of the general formula (IV) is obtained by a substitution reaction or a Mitsunobu reaction of the compound of the general formula (V). The substitution reaction can be carried out by treating a benzyl halide or mesylate of the general formula (V) with a phenol derivative in the presence of a base such as potassium carbonate, sodium hydride, sodium ethoxide, or butoxypotassium, in a compatible solvent such as DMF, water, acetone, acetonitrile, dichloromethane, or a mixture thereof, at a suitable temperature, preferably a temperature between 0° C. and a boiling point of the solvent. The Mitsunobu reaction can be carried out by using a benzyl alcohol of the general formula (V), a phenol derivative, and a triphenylphosphine in a compatible solvent such as DMF, THF, acetonitrile, dichloromethane, or a mixture thereof, in the presence of DEAD (diethyl azodicarboxylate), DIAD (diisopropyl azodicarboxylate), DPPA (diphenylphosphoryl azide), or the like, at a suitable temperature, preferably a temperature between 0° C. and a boiling point of the solvent.

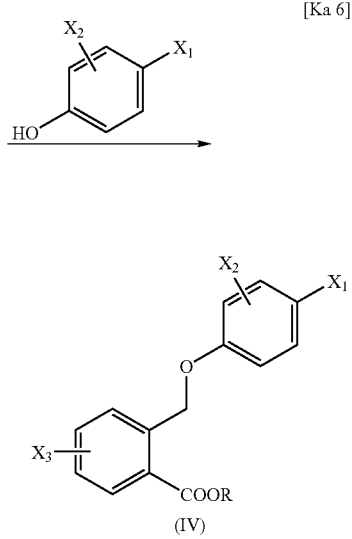

$Y =$ —OH, —OMs, —Br, —Cl

The compounds represented by the general formulas (I) and (I') mentioned above embrace, in a case where a pharmaceutically acceptable salt thereof is present, various kinds of salts thereof, and include, for example, addition salts with an acid such as hydrochloric acid, oxalic acid, fumaric acid, p-toluenesulfonic acid, maleic acid, succinic acid, acetic acid, citric acid, tartaric acid, carbonic acid, or nitric acid. In addition, the compounds can embrace salts of carboxyl group, and suitable alkali metal salt of sodium, potassium, calcium and the like. These salts can be produced from each compound in a free form, or converted reversibly, in accordance with a known method. In addition, in a case where the compounds are present in the state of a steric isomer such as a cis-trans isomer, an optical isomer or a coordination isomer, or a hydrate or a metal complex compound, the present invention embraces any of steric isomers, hydrates, and complex compounds.

The compound of the present invention can be combined with a suitable pharmaceutical carrier or diluent to form a medicament. Also, the compound can be produced into preparations by any ordinary methods, and the compounds can be produced into formulations as an orally administered agent such as a tablet, a capsule, a fine powder, or a liquid, or as a parenterally administered agent for subcutaneous administration, intramuscular administration, intrarectal administration, or intranasal administration. In the prescription, the compound of the present invention may be used in the form of a pharmaceutically acceptable salt thereof, and the compounds can be used alone or in a proper combination, and further, a blending agent with another pharmaceutically active ingredient.

The orally administered preparation can be used directly, or in a proper combination with a suitable additive, for example, a conventional excipient such as lactose, mannitol, corn starch, or potato starch, together with a binder such as a crystalline cellulose, a cellulose derivative, gum arabic, corn starch, or gelatin, a disintegrant such as corn starch, potato starch, carboxymethyl cellulose potassium, a lubricant such as talc or magnesium stearate, and other additive such as a filler, a wetting agent, a buffer, a preservative, or perfume, and the like to produce a tablet, a powder, a granule, or a capsule.

In addition, the compound can be produced into preparations in a dosage form other than above that is optimal for the treatment depending upon the kinds of the disease and the patients, including, for example, externally administered agents, such as injections, suppositories, inhalants, aerosols, syrups, instillations, and ointments, and the like.

The desired dose for the compound of the present invention may vary depending upon the subject to be administered, the dose form, the administration method, the administration time period, and the like. In order to obtain a desired effect, the compound of the present invention can be generally orally administered in an amount of from 0.5 to 1000 mg, and preferably from 1 to 500 mg, for adult, at once or in several divided administrations per day. In the case of the parenteral administration (for example, an injection), the daily dose is preferably from one-third to one-tenth the dose level for each of the doses mentioned above.

EXAMPLES

Next, the present invention will be specifically described hereinbelow by the Examples, without intending to limit the scope of the present invention thereto.

Starting raw materials can be purchased from Aldrich Chemical Company Incorporated, Tokyo Chemical Industry Co., Ltd., and the like. A melting point was determined by placing a sample in a glass capillary tube, and measuring a melting point with Yamato Scientific, Model MP-21, a melting point measuring instrument. An optical rotation was determined with JASCO Corporation, Model DP-140, an optical rotation measuring instrument. $^1$H-NMR was measured with Bruker, Model ARX500, a magnetic resonance analyzer, in which chemical shift was expressed in ppm, using TMS added as an internal standard ($\delta=0$ ppm) as a standard. Silica gel column chromatography was performed using silica gel BW-127ZH for chromatography (FUJI SILYSIA CHEMICAL LTD.). Thin-layer chromatography was performed using silica gel F254 (Merck, No. 5715), in which detection was made using a UV lamp and a 5% phosphomolybdic acid-ethanol color development reagent. As for reagents and solvents, commercially available products are directly used.

Example 1

Production of Methyl 2-(4-Bromophenoxymethyl)benzoate

Potassium carbonate (152 g, 1.1 mol) and 4-bromophenol (95.2 g, 550 mmol) were added to a DMF (500 mL) solution of methyl 2-bromomethylbenzoate (115 g, 500 mmol), and the mixture was stirred overnight at room temperature. Water was added to the reaction mixture, and the product was extracted with ethyl acetate. An organic layer was washed with a saturated sodium chloride solution, and dried over anhydrous sodium sulfate, and thereafter the solvents were distilled off under a reduced pressure. The residue was purified by column chromatography (hexane-toluene=1:1), to give 139 g (86%) of the captioned compound in the form of a colorless oily product.

$^1$H-NMR (DMSO-d$_6$) $\delta$: 3.84 (s, 3H), 5.39 (s, 2H), 6.91-6.95 (m, 2H), 7.08-7.13 (m, 2H), 7.44-7.49 (m, 1H), 7.62-7.66 (m, 2H), 7.89-7.93 (m, 1H).

Example 2

Production of Methyl 2-(4-Bromophenoxymethyl)benzoic Acid

A 2 mol/L aqueous sodium hydroxide solution (250 mL) was added to a methanol (1 L) solution of methyl 2-(4-bromophenoxymethyl)-benzoate (139 g, 432 mmol), and the mixture was stirred overnight while heating under reflux. Methanol was distilled off under a reduced pressure, and a 6 mol/L hydrochloric acid was added to the residue obtained to precipitate the crystals, and the precipitated crystals were collected by filtration, and sufficiently washed with water. The crystals were dried over phosphorus pentoxide at 50° C., to give 112 g (84%) of the captioned compound.

Mp. 177°-179° C. $^1$H-NMR (DMSO-d$_6$) $\delta$: 5.45 (s, 2H), 6.95-7.94 (m, 8H), 13.08 (brs, 1H).

Example 3

Production of 2-Bromo-6H-dibenz[b,e]oxepin-11-one

Trifluoroacetic anhydride (56.0 mL, 400 mmol) was added dropwise to a dichloromethane (500 mL) solution of 2-(4-bromophenoxymethyl)benzoic acid (112 g, 364 mmol) at room temperature. The mixture was stirred at room temperature for 2 hour, BF$_3$.OEt$_2$ (10 mL, 169.3 mmol) was then added thereto, and the mixture was stirred at room temperature for additional 2 hours. The reaction mixture was washed with a saturated aqueous sodium bicarbonate solution, and then with a saturated sodium chloride solution, the washed mixture was then dried over anhydrous sodium sulfate, and the solvents were distilled off under a reduce pressure. The residue was purified by column chromatography (hexane-ethyl acetate=3:2), to give 96.0 g (91%) of the captioned compound in the form of crystals.

Mp. 131°-133° C. $^1$H-NMR (DMSO-d$_6$) $\delta$: 5.34 (s, 2H), 7.10-7.12 (m, 1H), 7.54-7.60 (m, 2H), 7.68-7.81 (m, 3H), 8.15-8.16 (m, 1H).

Example 4

Production of 2-Bromo-11-(1-methylpiperidin-4-yl)-6,11-dihydrobenz[b,e]oxepin-11-ol A THF solution of 2-bromo-6H-dibenz[b,e]oxepin-11-one (71.0 g, 246 mmol) was added dropwise to a Grignard reagent prepared from 4-chloro-N-methylpiperidine (40.0 g, 300 mmol), the metal magnesium (7.89 g, 300 mmol), dibromoethane (0.1 mL), and THF (300 mL). After the termination of dropwise addition, the reaction mixture was stirred at room temperature for 2 hours. A saturated aqueous ammonium chloride solution was added to the solution to stop the reaction, and thereafter the product was extracted with ethyl acetate. An organic layer was washed with a saturated sodium chloride solution, and dried over anhydrous sodium sulfate. The solvents were distilled off under a reduced pressure, and the residue was purified by silica gel chromatography (hexane-ethyl acetate=3:2), to give 77.4 g (81%) of the captioned compound.

Mp. 194°-196° C. $^1$H-NMR (DMSO-d$_6$) $\delta$: 0.84-0.88 (m, 1H), 0.99-1.01 (m, 1H), 1.44-1.66 (m, 4H), 2.06 (s, 3H), 2.18-2.20 (m, 1H), 2.69-2.71 (m, 2H), 4.94 (d, J=15.8 Hz, 1H), 5.50 (d, J=15.8 Hz, 1H), 5.72 (s, 1H), 7.02-7.04 (m, 2H), 7.20-7.27 (m, 2H), 7.41-7.48 (m, 1H), 7.73-7.76 (m, 2H).

Example 5

Production of 4-(2-Bromo-6H-dibenz[b,e]oxepin-11-ylidene)-1-methylpiperidine

A TFA (150 mL) solution of 2-bromo-11-(1-methylpiperidin-4-yl)-6,11-dihydrodibenz[b,e]oxepin-11-ol (21.7 g, 56.0 mmol) was stirred overnight at room temperature. The solvent was distilled off under a reduced pressure, a 10% aqueous potassium carbonate solution was then added to the residue to neutralize, and the product was extracted with ethyl acetate. The extract was dried over anhydrous sodium sulfate, the solvent was then distilled off under a reduced pressure, and the reside was purified by column chromatography (chloroform-methanol=9:1), to give 15.1 g (73%) of the captioned compound in the form of crystals.

Mp. 131°-132° C. $^1$H-NMR (DMSO-$d_6$) δ: 1.95-2.61 (m, 1H), 4.90 (d, J=14.1 Hz, 1H), 5.58 (d, J=14.1 Hz, 1H), 6.68-7.49 (m, 7H).

Example 6

Production of 11-(1-Methylpiperidin-4-ylidene)-6,11-dihydrodibenz[b,e]oxepin-2-carbonitrile [Compound 5]

Zn(CN)$_2$ (4.70 g, 40.0 mmol), Pd$_2$(dba)$_3$ (0.23 g, 0.25 mmol), and DPPF (0.30 g, 0.50 mmol) were added to a DMF (100 mL) solution of 4-(2-bromo-6H-dibenz[b,e]oxepin-11-ylidene)-1-methylpiperidine (14.8 g, 40.0 mmol) in an argon atmosphere, and the mixture was stirred overnight at 80° C. Insoluble matters were filtered off, a saturated sodium chloride solution (50 mL) was then added to the filtrate, and the product was extracted with ethyl acetate. The solvent was distilled off under a reduced pressure, and thereafter the residue was purified by silica gel column chromatography (chloroform-methanol=9:1), to give 9.14 g (72%) of the captioned compound in the form of crystals.

Mp. 134°-136° C. MS (EI): m/z 316 [M$^+$]. $^1$H-NMR (DMSO-$d_6$) δ: 1.95-2.65 (m, 11H), 4.99 (d, J=12.1 Hz, 1H), 5.69 (d, J=12.1 Hz, 1H), 6.88 (d, J=8.6 Hz, 1H), 7.20-7.57 (m, 6H).

Example 7

Production of 11-(1-Methylpiperidin-4-ylidene)-6,11-dihydrodibenz[b,e]oxepin-2-carboxylic Acid [Compound 1]

A 2 mol/L aqueous sodium hydroxide solution (250 mL) was added to an ethanol (100 mL) solution of 11-(1-methylpiperidin-4-ylidene)-6,11-dihydrodibenz[b,e]oxepin-2-carbonitrile [Compound 5](5.0 g, 15.8 mmol), and the mixture was stirred overnight while heating under reflux. Methanol was distilled off under a reduced pressure, a 6 mol/L hydrochloric acid was added to the residue obtained to precipitate crystals, and the precipitated crystals were collected by filtration, and sufficiently washed with water. The washed crystals were dried over phosphorus pentoxide at 50° C. under a reduced pressure, to give 4.1 g (77%) of the captioned compound in the form of white crystals.

Mp. 205°-210° C. $^1$H-NMR (DMSO-$d_6$) δ: 1.06 (t, J=7.0 Hz, 3H), 2.07-2.65 (m, 11H), 3.44 (q, J=7.0 Hz, 2H), 4.95 (d, J=12.1 Hz, 1H), 5.67 (d, J=12.1 Hz, 1H), 6.78 (d, J=8.6 Hz, 1H), 7.20-7.67 (m, 6H).

Compounds other than those mentioned above, i.e. Compounds 2 through 4 and Compounds 6 through 43 listed previously, were produced in the same manner in accordance with the methods described in the above-mentioned Examples, using an appropriate starting raw material in place of methyl 2-bromomethylbenzoate, the starting raw material in Example 1. The data of physical properties for the compounds of the present invention thus obtained are shown in Tables 1 through 5.

TABLE 1

| Compound No. | Properties |
| --- | --- |
| Compound 2 | Mp. 270° C. (decomp.). $^1$H-NMR (DMSO-$d_6$) δ: 1.29 (t, J = 7.0 Hz, 3H), 2.48-3.79 (m, 11H), 4.25-4.29 (m, 2H), 4.98-5.02 (m, 1H), 5.69-5.85 (m, 1H), 6.84-7.73 (m, 7H), 11.1 (brs, 1H). |
| Compound 3 | Mp. 175°-178° C. $^1$H-NMR (DMSO-$d_6$) δ: 1.16-1.21 (m, 3H), 1.98-2.61 (m, 11H), 3.93-4.11 (m, 4H), 4.94 (d, J = 14.1 Hz, 1H), 5.63 (d, J = 14.1 Hz, 1H), 6.78-7.65 (m, 7H), 8.74 (m, 1H). |
| Compound 4 | Mp. 131°-132° C. $^1$H-NMR (DMSO-$d_6$) δ: 1.95-2.61 (m, 11H), 4.90 (d, J = 14.1 Hz, 1H), 5.58 (d, J = 14.1 Hz, 1H), 6.68-7.49 (m, 7H). |
| Compound 6 | Mp. 244° C. (decomp.). $^1$H-NMR (DMSO-$d_6$) δ: 1.88-2.67 (m, 11H), 3.70 (s, 3H), 4.92 (d, J = 12.1 Hz, 1H), 5.63 (d, J = 12.1 Hz, 1H), 6.43 (d, J = 15.9 Hz, 1H), 6.75 (d, J = 8.6 Hz, 1H), 7.13-7.58 (m, 7H). |
| Compound 7 | Mp. 145° C. (decomp.). $^1$H-NMR (DMSO-$d_6$) δ: 2.38-3.34 (m, 11H), 4.94 (d, J = 9.3 Hz, 1H), 5.71 (d, J = 9.3 Hz, 1H), 6.36 (d, J = 14.3 Hz, 1H), 6.77-6.78 (m, 1H), 7.19-7.69 (m, 8H), 11.54-11.83 (br, 1H). |
| Compound 8 | Mp. 225° C. (decomp.). MS (EI): m/z 359 [M$^+$]. $^1$H-NMR (DMSO-$d_6$) δ: 2.37-3.12 (m, 11H), 4.93 (d, J = 14.1 Hz, 1H), 5.69 (d, J = 14.1 Hz, 1H), 6.83 (d, J = 7.4 Hz, 1H), 7.20-7.77 (m, 6H). |
| Compound 9 | Mp. 145°-148° C. $^1$H-NMR (DMSO-$d_6$) δ: 1.39 (s, 9H), 2.02-2.60 (m, 11H), 3.93-4.03 (m, 2H), 4.84 (d, J = 14.1 Hz, 1H), 5.54 (d, J = 14.1 Hz, 1H), 6.64-7.46 (m, 8H). |
| Compound 10 | Mp. 207°-209° C. MS (EI): m/z 362 [M$^+$], 345. $^1$H-NMR (DMSO-$d_6$) δ: 1.83 (s, 3H), 2.02-2.61 (m, 11H), 4.05-4.16 (m, 2H), 4.84 (d, J = 12.1 Hz, 1H), 5.54 (d, J = 12.1 Hz, 1H), 6.65 (d, J = 7.1 Hz, 1H), 6.88-7.46 (m, 6H), 8.23 (m, 1H). |

TABLE 2

| Compound No. | Properties |
| --- | --- |
| Compound 11 | Mp. 140° C. (decomp.). $^1$H-NMR (DMSO-$d_6$) δ: 1.98-2.61 (m, 13H), 3.46-3.51 (m, 1H), 3.67-3.71 (m, 1H), 4.82 (d, J = 14.1 Hz, 1H), 5.52 (d, J = 14.1 Hz, 1H), 6.64 (d, J = 7.1 Hz, 1H), 6.95 (s, 1H), 7.04-7.45 (m, 5H), 9.71 (s, 1H). |
| Compound 12 | Mp. 127°-128° C. $^1$H-NMR (DMSO-$d_6$) δ: 1.98-2.61 (m, 11H), 4.90 (d, J = 14.1 Hz, 1H), 5.59 (d, J = 14.1 Hz, 1H), 6.92-7.49 (m, 7H). |
| Compound 13 | Mp. 175°-176° C. MS (EI) m/z: 316 [M$^+$]. $^1$H-NMR (DMSO-$d_6$) δ: 2.00-2.64 (m, 11H), 4.95 (d, J = 14.1 Hz, 1H), 5.65 (d, J = 14.1 Hz, 1H), 7.17-7.51 (m, 7H). |
| Compound 14 | Mp. 135°-136° C. MS (EI): m/z 392 [M$^+$], 244. $^1$H-NMR (DMSO-$d_6$) δ: 1.15 (t, J = 7.4 Hz, 3H), 2.03-2.59 (m, 11H), 3.96-4.08 (m, 4H), 4.82 (d, J = 14.1 Hz, 1H), 5.54 (d, J = 14.1 Hz, 1H), 6.65-7.47 (m, 8H). |
| Compound 15 | Mp. 195°-196° C. $^1$H-NMR (DMSO-$d_6$) δ: 1.98-2.61 (m, 14H), 4.82 (d, J = 14.1 Hz, 1H), 5.52 (d, J = 14.1 Hz, 1H), 6.63-7.45 (m, 7H), 9.71 (s, 1H). |
| Compound 16 | Mp. 133°-134° C. $^1$H-NMR (DMSO-$d_6$) δ: 1.98-2.61 (m, 14H), 4.82 (d, J = 14.1 Hz, 1H), 5.52 (d, J = 14.1 Hz, 1H), 6.63-7.45 (m, 7H), 9.71 (s, 1H). |
| Compound 17 | Mp. 183° C. (decomp.). MS (EI): m/z 349 [M$^+$], 332. $^1$H-NMR (DMSO-$d_6$) δ: 2.05-2.61 (m, 11H), 4.80 (d, J = 12.1 Hz, 1H), 5.50 (d, J = 12.1 Hz, 1H), 5.67 (s, 2H), 6.58 (d, J = 7.1 Hz, 1H), 7.04-7.44 (m, 6H), 8.27 (s, 1H). |
| Compound 18 | Mp. 208°-212° C. MS (EI): m/z 335 [M$^+$]. $^1$H-NMR (DMSO-$d_6$) δ: 1.13-2.71 (m, 11H), 4.92 (d, J = 12.1 Hz, 1H), 5.64 (d, J = 12.1 Hz, 1H), 7.09 (d, J = 8.6 Hz, 1H), 7.16-7.50 (m, 6H). |
| Compound 19 | Mp. 234°-236° C. MS (EI): m/z 378 [M$^+$], 361. $^1$H-NMR (DMSO-$d_6$) δ: 1.96-2.65 (m, 11H), 3.27-3.33 (m, 2H), 3.46-3.50 (m, 2H), 4.67-4.69 (m, 1H), 4.93 (d, J = 14.1 Hz, 1H), 5.64 (d, J = 14.1 Hz, 1H), 6.75 (d, J = 7.4 Hz, 1H), 7.17-7.64 (m, 6H), 8.22-8.24 (m, 1H). |

TABLE 3

| Compound No. | Properties |
| --- | --- |
| Compound 20 | Mp. 218°-219° C. MS (EI): m/z 424 [M$^+$]. $^1$H-NMR (DMSO-$d_6$) δ: 2.06-2.51 (m, 11H), 4.29-4.43 (m, 2H), 4.84 (d, J = 14.1 Hz, 1H), 5.54 (d, J = 14.1 Hz, 1H), 6.66-7.88 (m, 12H), 8.96 (m, 1H). |
| Compound 21 | Mp. 140°-143° C. $^1$H-NMR (DMSO-$d_6$) δ: 1.99-2.01 (m, 1H), 2.16-2.23 (m, 5H), 2.29-2.31 (m, 1H), 2.52-2.54 (m, 3H), 2.62-2.64 (m, 1H), 4.35-4.36 (m, 2H), 4.85 (d, J = 14.1 Hz, 1H), 5.00-5.02 (m, 1H), 5.56 (d, J = 14.1 Hz, 1H), 6.65-6.67 (m, 1H), 6.95-7.47 (m, 6H) |
| Compound 22 | Mp. 118° C. (dec.). $^1$H-NMR (DMSO-$d_6$) δ: 1.98-2.65 (m, 11H), 4.05-4.07 (m, 2H), 4.76-4.78 (m, 1H), 4.87 (d, J = 11.7 Hz, 1H), 5.57 (d, J = 11.7 Hz, 1H), 6.13-6.19 (m, 1H), 6.41-6.44 (m, 1H), 6.66-6.68 (m, 1H), 7.00 (s, 1H), 7.15-7.48 (m, 5H). |
| Compound 23 | Mp. 157°-160° C. $^1$H-NMR (DMSO-$d_6$) δ: 2.01-2.66 (m, 11H), 5.00 (d, J = 12.1 Hz, 1H), 5.70 (d, J = 12.1 Hz, 1H), 6.89-7.66 (m, 7H), 9.82 (s, 1H). |
| Compound 24 | Mp. 226° C. (dec.). MS (EI): m/z 350.2 [M$^+$ + 1], 305.3. $^1$H-NMR (DMSO-$d_6$) δ: 2.04-2.64 (m, 11H), 3.38-3.46 (m, 2H), 4.85 (d, J = 12.1 Hz, 1H), 5.56 (d, J = 12.1 Hz, 1H), 6.63-7.47 (m, 7H). |
| Compound 25 | MS (EI): m/z 381.1 [M$^+$], 283.2. $^1$H-NMR (DMSO-$d_6$) δ: 1.18 (t, J = 7.1 Hz, 3H), 1.94-2.81 (m, 13H), 3.21-3.24 (m, 2H), 3.77 (s, 2H), 4.04 (q, J = 7.1 Hz, 2H), 6.62 (s, 1H), 6.98-6.99 (m, 1H), 7.14-7.19 (m, 2H), 7.27-7.29 (m, 1H). |
| Compound 26 | Mp. 144° C. (dec.). $^1$H-NMR (DMSO-$d_6$) δ: 2.02-2.63 (m, 15H), 4.06-4.18 (m, 2H), 4.84 (d, J = 12.1 Hz, 1H), 5.56 (d, J = 12.1 Hz, 1H), 6.64-7.46 (m, 7H), 8.26-8.28 (m, 1H). |

TABLE 4

| Compound No. | Properties |
| --- | --- |
| Compound 27 | Mp. 150°-152° C. $^1$H-NMR (DMSO-$d_6$) δ: 1.16 (t, J = 7.1 Hz, 3H), 2.00-2.62 (m, 15H), 4.04 (q, J = 7.1 Hz, 2H), 4.14-4.18 (m, 2H), 4.84 (d, J = 12.1 Hz, 1H), 5.56 (d, J = 12.1 Hz, 1H), 6.64-7.46 (m, 7H), 8.26-8.28 (m, 1H). |
| Compound 28 | Mp. 251° C. (dec.). MS (EI): m/z 336.1 [M$^+$ + 1]. $^1$H-NMR (DMSO-$d_6$) δ: 1.30-1.90 (m, 11H), 4.56 (d, J = 12.1 Hz, 1H), 5.28 (d, J = 12.1 Hz, 1H), 6.25-7.75 (m, 5H), 7.58-7.66 (m, 2H). |

TABLE 4-continued

| Compound No. | Properties |
| --- | --- |
| Compound 29 | Mp. 124° C. (dec.). $^1$H-NMR (DMSO-$d_6$) δ: 1.26 (t, J = 7.1 Hz, 3H), 2.03-2.65 (m, 11H), 4.22 (q, J = 7.1 Hz, 2H), 4.96 (d, J = 12.1 Hz, 1H), 5.65 (d, J = 12.1 Hz, 1H), 6.90-7.47 (m, 7H). |
| Compound 30 | $^1$H-NMR (DMSO-$d_6$) δ: 1.99-2.00 (m, 1H), 2.16 (s, 3H), 2.16-2.22 (m, 2H), 2.30-2.32 (m, 1H), 2.46-2.53 (m, 3H), 2.60-2.62 (m, 1H), 5.03 (d, J = 12.3 Hz, 1H), 5.68 (d, J = 12.3 Hz, 1H), 6.77-6.78 (m, 1H), 7.00-7.02 (m, 1H), 7.16-7.17 (m, 1H), 7.32-7.52 (m, 4H). |
| Compound 31 | Mp. 126°-127° C. $^1$H-NMR (DMSO-$d_6$) δ: 1.25 (t, J = 7.1 Hz, 3H), 1.97-2.62 (m, 11H), 4.18 (q, J = 7.1 Hz, 2H), 5.08 (d, J = 12.1 Hz, 1H), 5.70 (d, J = 12.1 Hz, 1H), 6.49 (d, J = 16.1 Hz, 1H), 6.87-7.59 (m, 7H), 7.86 (d, J = 16.1 Hz, 1H). |
| Compound 32 | Mp. 188° C. (dec.). $^1$H-NMR (DMSO-$d_6$) δ: 2.00-2.64 (m, 11H), 5.07 (d, J = 12.1 Hz, 1H), 5.69 (d, J = 12.1 Hz, 1H), 6.39 (d, J = 16.1 Hz, 1H), 6.87-7.55 (m, 7H), 7.81 (d, J = 16.1 Hz, 1H), 11.85-12.43 (br, 1H). |
| Compound 33 | Mp. 210° C. (dec.). MS (EI): m/z 336.1 [M$^+$ + 1]. $^1$H-NMR (DMSO-$d_6$) δ: 1.30-1.90 (m, 11H), 4.56 (d, J = 12.1 Hz, 1H), 5.28 (d, J = 12.1 Hz, 1H), 6.25-7.75 (m, 5H), 7.58-7.66 (m, 2H). |
| Compound 34 | Mp. 175°-178° C. $^1$H-NMR (DMSO-$d_6$) δ: 1.99-2.63 (m, 11H), 5.12 (d, J = 12.1 Hz, 1H), 5.28 (d, J = 12.1 Hz, 1H), 6.97-7.59 (m, 7H). |

TABLE 5

| Compound No. | Properties |
| --- | --- |
| Compound 35 | Mp. 173°-175° C. $^1$H-NMR (DMSO-$d_6$) δ: 1.24 (t, J = 7.1 Hz, 3H), 1.97-2.65 (m, 11H), 4.16 (q, J = 7.1 Hz, 2H), 4.90 (d, J = 12.1 Hz, 1H), 5.60 (d, J = 12.1 Hz, 1H), 6.52 (d, J = 16.1 Hz, 1H), 7.02-7.52 (m, 8H). |
| Compound 36 | Mp. 124° C. (dec.). $^1$H-NMR (DMSO-$d_6$) δ: 1.26 (t, J = 7.1 Hz, 3H), 2.03-2.65 (m, 11H), 4.22 (q, J = 7.1 Hz, 2H), 4.96 (d, J = 12.1 Hz, 1H), 5.65 (d, J = 12.1 Hz, 1H), 6.90-7.47 (m, 7H). |
| Compound 37 | Mp. 233° C. (dec.). $^1$H-NMR (DMSO-$d_6$) δ: 2.03-2.65 (m, 11H), 4.96 (d, J = 12.1 Hz, 1H), 5.65 (d, J = 12.1 Hz, 1H), 6.90-7.47 (m, 7H). |
| Compound 38 | $^1$H-NMR (DMSO-$d_6$) δ: 2.25-2.99 (m, 11H), 3.35-3.44 (m, 2H), 4.88-4.91 (m, 1H), 5.55-5.72 (m, 1H), 6.65 (s, 1H), 6.74-7.52 (m, 6H), 10.30-10.40 (m, 1H), 12.31 (brs, 1H). |
| Compound 39 | $^1$H-NMR (DMSO-$d_6$) δ: 1.99-2.01 (m, 1H), 2.16-2.33 (m, 6H), 2.46-2.64 (m, 4H), 4.66 (t, J = 5.1 Hz, 1H), 4.92 (d, J = 12.2 Hz, 1H), 5.62 (d, J = 12.2 Hz, 1H), 7.06-7.50 (m, 7H), 8.28 (t, J = 5.1 Hz, 1H). |
| Compound 40 | Mp. 184°-186° C. $^1$H-NMR (DMSO-$d_6$) δ: 1.97-2.65 (m, 11H), 3.36-3.51 (m, 4H), 4.71 (t, J = 5.7 Hz, 1H), 4.92 (d, J = 12.2 Hz, 1H), 5.61 (d, J = 12.2 Hz, 1H), 6.72-7.24 (m, 5H), 7.82-7.84 (m, 1H), 7.95 (s, 1H), 8.41-8.44 (m, 1H). |
| Compound 41 | $^1$H-NMR (DMSO-$d_6$) δ: 1.29-1.33 (m, 3H), 2.63-2.99 (m, 8H), 3.57-3.59 (m, 4H), 4.84-4.90 (m, 1H), 5.53-5.71 (m, 1H), 6.68-7.51 (m, 7H), 10.83-10.89 (m, 1H), 12.27 (brs, 1H). |
| Compound 42 | $^1$H-NMR (DMSO-$d_6$) δ: 1.96-2.33 (m, 7H), 2.52-2.65 (m, 2H), 3.29-3.51 (m, 6H), 4.70 (t, J = 5.1 Hz, 1H), 4.92 (d, J = 12.2 Hz, 1H), 5.59 (d, J = 12.2 Hz, 1H), 6.72-7.79 (m, 7H), 8.46 (t, J = 5.1 Hz, 1H). |
| Compound 43 | Mp. undeterminable. MS (EI): m/z 364 [M$^+$ + 1]. $^1$H-NMR (DMSO-$d_6$) δ: 2.30-2.91 (m, 15H), 4.84 (d, J = 12.2 Hz, 1H), 5.58 (d, J = 12.2 Hz, 1H), 6.63-6.64 (m, 1H), 6.85 (s, 1H), 6.96-7.47 (m, 5H). |

Example 8

Rat Histamine-Induced Vascular Hyperpermeability Reaction (in Vivo Antihistamine Action)

An SD male rat (SPF) of 180 g in weight was previously fed for one week or more by allowing the rat to take a solid feed and tap water ad libitum, under the environment setting of a temperature of 22° C., humidity of 55% and an artificial illumination of 12 hours a day (light phase 8 am to 8 pm), and the rat was fasted overnight to be used for the experiment. Histamine-dihydrochloride (hereinafter referred to as histamine) and Evans Blue were used by dissolving each in physiological saline upon use. A substance to be tested was dissolved in water for injection or suspended in 0.5% carboxymethyl cellulose sodium, and the rat was orally administered with the solution or suspension (dose volume: 5 mL/kg body weight). After 1 hour from the administration, the physiological saline and the histamine solution were each intracutaneously injected to two locations (20 µg/0.05 ml/location) each on a back part of the rat of which hair was sheared with an electric clipper while anesthetizing with an ether. A 0.5% Evans Blue-containing physiological saline was injected intravenously to the tail (1 mL/200 g body weight) of the rat immediately before the intracutaneous injection of the histamine.

After 30 minutes, the animal was decapitated, and allowed to bleed lethally, and the skin was removed to measure an amount of leaked pigment in the blue-stained portion. The measurement of the amount of leaked pigment was carried out as follows. Skins of the pigment leaking site were cut out at two locations, 1 mL of a 2 mol/L aqueous potassium hydroxide solution was added thereto in a test tube, and the test tube was allowed to stand overnight at 37° C. to dissolve. Thereafter, 6 mL of a 1:3 mixed solution of 0.67 mol/L phosphoric acid and acetone was added to the solution, and the mixture was vigorously shaken for 10 minutes. Thereafter, the mixture was filtered, and the absorbance of the filtrate at 620 nm was measured. The absorbance obtained from the two locations of the sites injected with physiological saline, obtained as blank value, was used for a compensation. The amount of leaked pigment was calculated from the calibration curve of Evans Blue at 620 nm.

One example of the results is shown in Table 6. The compound of the present invention showed a very potent antagonistic activity in the rat histamine-induced vascular hyperpermeability reaction.

TABLE 6

| Compound No. | $ED_{50}$ (mg/kg) |
| --- | --- |
| Compound 1 | 0.046 |
| Compound 7 | 0.3 |
| Compound 17 | 0.62 |
| Compound 24 | 0.03 |
| Compound 43 | 0.1 |
| Ketotifen | 0.54 |

Example 9

Murine Intracranial H1 Receptor Content (ex Vivo)

A 6-week-old ICR male rat was previously fed for one week or more by allowing the rat to take a solid feed and tap water ad libitum, under the environment setting of a temperature of 22° C., humidity of 55% and an artificial illumination of 12 hours a day, and the rat was fasted overnight to be used for the experiment. A substance to be tested was dissolved with water for injection or suspended in 0.5% carboxymethyl cellulose solution, and the solution or suspension was orally administered to the rat (dose volume: 0.1 mL/10 g body weight). After 1 hour from the oral administration, the rat was decapitated, and the entire brain, except for cerebellum and medulla oblongatae, was rapidly excised. The excised brain tissue was homogenized with Polytron (manufactured by Kinematica) in an ice-cooled 50 mmol/L phosphate buffered saline (pH 7.4, 100 mg/1.9 mL).

To a test tube for reaction (TPX-Tube) were added 180 µL of the brain homogenate, and 10 µL of $^3$H-pyrilamine solution (final concentration: 2 nmol/L) and 10 µL of a non-labeled pyrilamine solution (final concentration: 200 µmol/L) or a 50 mmol/L phosphate buffered saline, and the mixture was incubated at room temperature for 45 minutes, and 2.0 mL of an ice-cooled, 50 mmol/L phosphate buffered saline was then added thereto to stop the reaction. The reaction mixture was filtered with a GF/B filter (manufactured by ADVANTEC), and the filtrate was placed in a vial and dried overnight at 60 degrees. After drying, 10 mL of a scintillater (AL-1, toluene-based, manufactured by DOJINDO LABORATORIES) was added to the product, and the disintegration per minute (dpm) was measured with a liquid scintillation counter (manufactured by Packard, U.S.A., TRI-CARB 2700TR) (5 minutes/vial).

One example of the results is shown in Table 7. In this experiment, the compound of the present invention require a high concentration for occupying the receptor in the brain, showing that the intracranial migration is low. It was shown from the results that the compound of the present invention alleviates side effects on the central nervous system, such as drowsiness.

TABLE 7

| Compound No. | $ID_{50}$ (mg/kg) |
| --- | --- |
| Compound 1 | 1.25 |
| Compound 7 | 1.32 |
| Compound 17 | 37.6 |
| Compound 24 | 1.60 |
| Compound 43 | <2.00 |
| Ketotifen | 0.51 |

From the results of Examples 8 and 9 mentioned above, the values obtained by dividing the ID50 (Table 7) of the intracranial receptor binding test by the ED50 (Table 6) of the histamine-induced vascular hyperpermeability reaction test are shown in Table 8. The larger the ID50 (Table 7) of the intracranial receptor binding test, the lower the intracranial migration, i.e. the smaller the side effects on the central nervous system, such as drowsiness; and the smaller the ED50 (Table 6) of the histamine-induced vascular hyperpermeability reaction test, the more potent the antihistamine action. Therefore, the value calculated by ID50, ED50 can serve as an index showing that the larger the calculated value, the more potent the antihistamine action and the smaller the side effects on the central nervous system, such as drowsiness. As shown in Table 8, the compound of the present invention shows a large value for a value calculated by ID50, ED50, as compared to an already existing antihistamine Ketotifen. Therefore, it can be said that the compound of the present invention has desired properties as a medicament that has a potent antihistamine action and smaller side effects on the central nervous system, such as drowsiness

TABLE 8

| Compound No. | $ID_{50}$ (mg/kg)/$ED_{50}$ (mg/kg) |
| --- | --- |
| Compound 1 | 27.2 |
| Compound 7 | 4.4 |
| Compound 17 | 60.6 |
| Compound 24 | 53.3 |
| Compound 43 | >20.0 |
| Ketotifen | 0.9 |

Industrial Applicability

As shown in Table 6, the oxepin derivative of the present invention shows a potent histamine receptor antagonistic activity. Further, as is clear from Table 7, the oxepin derivative shows a low intracranial migration even when subjecting an orally administered mouse to an intracranial receptor binding test, so that the oxepin derivative of the present invention is preferable from the aspect of alleviating side effects on the central nervous system, such as drowsiness. As is clear from the values of Table 8 for together evaluating both of these histamine receptor antagonistic activity and intracranial migration, the oxepin derivative or the present invention is a potent histamine receptor antagonistic substance, and has smaller side effects on the central nervous system, such as drowsiness; therefore, the oxepin derivative has properties suitable for a medicament, such as a desired antihistamine, so that the oxepin derivative is highly useful.

The invention claimed is:

1. An oxepin derivative, and salt thereof that are pharmaceutically acceptable, wherein the oxepin derivative is represented by the following general formula (I):

[Ka 7]

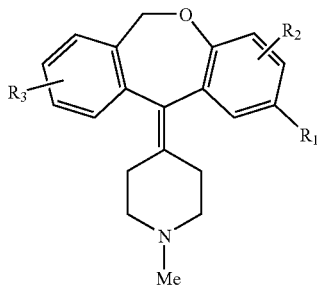

(I)

wherein $R_1$ is a hydrogen, a formyl, a carbonitrile, a tetrazolyl, a carboxyl, a carboxyalkyl, a hydroxyalkylaminocarbonyl, an alkoxycarbonylalkylaminocarbonyl, a hydroxyalkenyl, a carboxyalkenyl, an alkoxycarbonylalkenyl, a ureido, an alkylcarbonylamino, or an aminoalkyl which may be substituted by one or two substituents selected from the following (a) to (e):
(a) an alkylcarbonyl;
(b) an alkoxycarbonyl;
(c) a carboxyalkylcarbonyl;
(d) an alkoxycarbonylalkylcarbonyl; and
(e) a benzoyl;
$R_2$ is a hydrogen, and $R_3$ is a substituent at 8-position or 9-position of the dibenzoxepin backbone, and stands for a hydrogen, a carboxyl, an alkoxycarbonyl, or a hydroxyalkylaminocarbonyl,
wherein one of $R_1$, and $R_3$ stands for the substituent as defined above other than the hydrogen, and the remaining one stands for a hydrogen.

2. The oxepin derivative, and salt thereof that are pharmaceutically acceptable according to claim 1, wherein $R_3$ is a hydrogen.

3. The oxepin derivative, and salt thereof that are pharmaceutically acceptable according to claim 2, wherein $R_1$ is a ureido group.

4. The oxepin derivative, and salt thereof that are pharmaceutically acceptable according to claim 2, wherein $R_1$ is a carboxyalkyl group.

5. The oxepin derivative, and salt thereof that are pharmaceutically acceptable according to claim 4, wherein $R_1$ is a carboxymethyl group.

6. The oxepin derivative, and salt thereof that are pharmaceutically acceptable according to claim 4, wherein $R_1$ is a carboxyethyl group.

7. The oxepin derivative, and salt thereof that are pharmaceutically acceptable according to claim 2, wherein $R_1$ is a carboxyl group.

8. A medicament comprising at least one member selected from the oxepin derivative, and salt thereof that are pharmaceutically acceptable as defined in claim 1.

9. An antihistamine comprising at least one member selected from an oxepin derivative, and salt thereof that are pharmaceutically acceptable as defined in claim 1.

10. The antihistamine of claim 9, wherein $R_3$ of the oxepin derivative, and salt thereof that are pharmaceutically acceptable, is a hydrogen.

11. The antihistamine of claim 10, wherein $R_1$ of the oxepin derivative, and salt thereof that are pharmaceutically acceptable, is a ureido group.

12. The antihistamine of claim 10, wherein $R_1$ of the oxepin derivative, and salt thereof that are pharmaceutically acceptable, is a carboxyalkyl group.

13. The antihistamine of claim 12, wherein the carboxyalkyl group is a carboxymethyl group.

14. The antihistamine of claim 12, wherein the carboxyalkyl group is a carboxyethyl group.

15. The antihistamine of claim 10, wherein $R_1$ of the oxepin derivative, and salt thereof that are pharmaceutically acceptable, is a carboxyl group.

* * * * *